(12) United States Patent
Beden et al.

(10) Patent No.: US 8,375,797 B2
(45) Date of Patent: Feb. 19, 2013

(54) METHOD FOR OPERATING A PRESSURE MEASURING UNIT, APPARATUS HAVING AT LEAST ONE PRESSURE MEASURING UNIT, DEVICE HAVING SUCH AN APPARATUS, AND USE OF A MEASURING CHAMBER

(75) Inventors: Josef Beden, Mainz-Kastel (DE); Itka Bado, Bad Homburg (DE); Patrick Spalt, Steinbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 212 days.

(21) Appl. No.: 13/055,558

(22) PCT Filed: Jul. 21, 2009

(86) PCT No.: PCT/EP2009/005292
§ 371 (c)(1),
(2), (4) Date: Jan. 24, 2011

(87) PCT Pub. No.: WO2010/009867
PCT Pub. Date: Jan. 28, 2010

(65) Prior Publication Data
US 2011/0120227 A1 May 26, 2011

(30) Foreign Application Priority Data
Jul. 22, 2008 (DE) .......................... 10 2008 034 154

(51) Int. Cl.
*G01L 9/00* (2006.01)
*A61B 8/00* (2006.01)
(52) U.S. Cl. .............................. 73/723; 73/715; 600/448
(58) Field of Classification Search .................. None
See application file for complete search history.

(56) References Cited

U.S. PATENT DOCUMENTS
5,614,677 A 3/1997 Wamsiedler et al.
(Continued)

FOREIGN PATENT DOCUMENTS
DE 29 30 869 C2 10/1986
DE 44 19 593 A1 12/1995
(Continued)

*Primary Examiner* — Lisa Caputo
*Assistant Examiner* — Jermaine Jenkins
(74) *Attorney, Agent, or Firm* — Jacobson Holman PLLC

(57) ABSTRACT

The present invention relates to a method for the operation of a pressure measuring device for the measurement of the pressure in a system through which fluid flows, in particular in an extracorporeal circuit of a medical unit, with the pressure measuring device having a measuring chamber which is bounded by a flexible membrane, through which fluid flows in the operation of the system or which is filled with fluid and also having a pressure sensor connected to the membrane for the purpose of pressure measurement, with the method including the following steps not requiring any intervention of the staff: a. increasing the pressure in the measuring chamber (12) to a pressure value at which the membrane (13) is at least slightly outwardly curved relative to the measuring chamber (12) in the state not connected to the pressure sensor (14) or determining such a pressure value; b: separating the membrane (13) of the measuring chamber (12) from the pressure sensor (14); c. joining together the membrane (13) of the measuring chamber (12) and of the pressure sensor (14) such that the membrane (13) of the measuring chamber (12) contacts the pressure sensor (14); and d. repeating the steps a. to c. at predetermined intervals and/or on the occurrence of an error case.

33 Claims, 2 Drawing Sheets

U.S. PATENT DOCUMENTS

Figure 1:
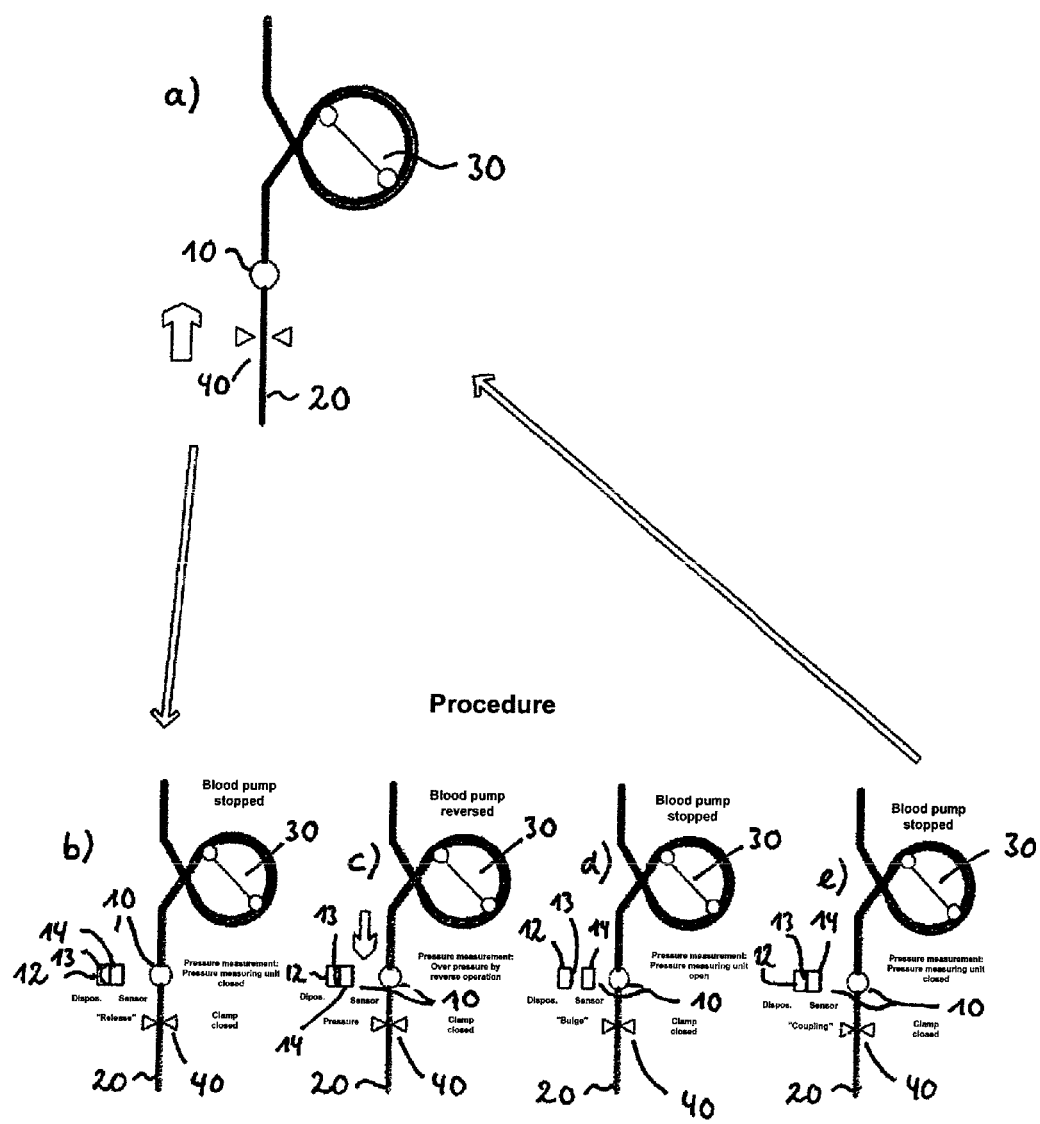

| | | | |
|---|---|---|---|
| 5,722,399 A * | 3/1998 | Chevallet et al. | 600/485 |
| 5,951,487 A * | 9/1999 | Brehmeier-Flick et al. | 600/561 |
| 6,044,691 A * | 4/2000 | Kenley et al. | 73/40.5 R |
| 6,280,632 B1 * | 8/2001 | Polaschegg | 210/739 |
| 6,484,383 B1 | 11/2002 | Herklotz | |
| 6,649,046 B2 * | 11/2003 | Chevallet | 210/90 |
| 6,804,991 B2 * | 10/2004 | Balschat et al. | 73/40.5 R |
| 6,880,404 B2 | 4/2005 | Überreiter | |
| 7,013,703 B2 * | 3/2006 | Derek et al. | 73/1.73 |
| 7,341,568 B2 * | 3/2008 | Zhang | 604/4.01 |
| 7,516,665 B2 * | 4/2009 | Teugels | 73/706 |
| 7,603,907 B2 * | 10/2009 | Reiter et al. | 73/715 |
| 7,748,275 B2 * | 7/2010 | Kouda et al. | 73/714 |
| 7,748,277 B2 * | 7/2010 | O'Brien et al. | 73/723 |
| 7,803,628 B2 * | 9/2010 | Glocker | 436/70 |
| 7,854,172 B2 * | 12/2010 | O'Brien et al. | 73/756 |
| 7,921,723 B2 * | 4/2011 | Reiter et al. | 73/715 |
| 8,113,060 B2 * | 2/2012 | Jonsson et al. | 73/756 |
| 8,156,817 B2 * | 4/2012 | Kaneko et al. | 73/728 |

FOREIGN PATENT DOCUMENTS

| | | |
|---|---|---|
| DE | 198 14 101 A1 | 10/1999 |
| DE | 100 32 616 A1 | 1/2002 |
| DE | 10 2006 048 785 A1 | 6/2008 |
| EP | 1 213 033 A1 | 6/2002 |
| GB | 2 029 579 A | 3/1980 |
| WO | WO 99/13926 A2 | 3/1999 |
| WO | WO 02/03854 A2 | 1/2002 |

* cited by examiner

METHOD FOR OPERATING A PRESSURE MEASURING UNIT, APPARATUS HAVING AT LEAST ONE PRESSURE MEASURING UNIT, DEVICE HAVING SUCH AN APPARATUS, AND USE OF A MEASURING CHAMBER

This is a national stage of PCT/EP09/005,292 filed Jul. 21, 2009 and published in English, which claims the priority of Germany number 10 2008 034 154.1 filed Jul. 22, 2008, hereby incorporated by reference.

The present invention relates to a method for the operation of a pressure measuring device for the measurement of the pressure in a system through which fluid flows, in particular in an extracorporeal circuit of a medical unit, with the pressure measuring device having a measuring chamber which is bounded by a flexible membrane, through which fluid flows in the operation of the system or which is filled with fluid and also having a pressure sensor connected to the membrane for the purpose of pressure measurement.

Such a method is known, for example, from U.S. Pat. No. 5,614,677. The pressure measuring device known from this reference serves the pressure measurement in an extracorporeal blood circuit. Blood flows through the measuring chamber in this connection. The measurement chamber is in contact with a pressure sensor via a flexible membrane.

To prevent a release of the membrane occurring where possible on too great a vacuum to prevent falsified pressure values or no pressure values at all from being obtained, it is proposed in U.S. Pat. No. 5,614,677 to match the named membrane of the measuring chamber and the pressure sensor as free of air as possible. A reliable measurement can be carried out at least in a certain vacuum range due to the corresponding adhesive effect.

A method of coupling a pump chamber to the operating fluid chamber of a membrane pump is known from U.S. Pat. No. 6,484,383 B1.

In so-called acute dialysis, the treatment of the patients takes place differently to the treatment of chronically sick dialysis patients who have to undergo hemodialysis treatment for approximately four to five hours every two to three days, almost continuously. It can occur in this respect that the treatment can last several days without interruption in dependence on the condition of the patient, for example in an intensive care unit. In such a case, it must accordingly be ensured over a comparatively long period that the pressure measuring device operates without problem and reliably.

It is therefore the underlying object of the present invention to further develop a method of the initially named kind such that the pressure detection also takes place reliably over a long period.

This object is solved by a method having the features of claim 1.

Provision is accordingly made for the method to include the following steps requiring no action of the staff:
a. increasing the pressure in the measuring chamber to a pressure value at which the membrane is at least slightly outwardly curved relative to the measuring chamber in the state not connected to the pressure sensor or determining such a pressure value;
b. separating the membrane of the measuring chamber from the pressure sensor;
c. joining together the membrane of the measurement chamber and of the pressure sensor such that the membrane of the measuring chamber contacts the pressure sensor; and
d. repeating the steps a. to c. at predetermined intervals and/or on the occurrence of an error case.

Provision is thus made in accordance with the invention for a mechanical recoupling of the measuring chamber or of its membrane to the pressure sensor at periodic intervals or on the occurrence of an error case, i.e. as required.

To be able to carry out a repeat coupling reliably, that is to be able to place the membrane of the measuring chamber correctly onto the pressure sensor, provision is made in accordance with the invention to produce such an overpressure in the measuring chamber that its membrane is curved at least slightly outwardly, that is, convexly. A reliable coupling of the membrane with the pressure sensor can take place in this state. There is otherwise the risk that the membrane will be pulled inwardly, that is, will be concavely deformed, by a negative pressure with an open pressure measuring device, which has the consequence that the pressure measurement deteriorates or fails under certain circumstances after the recoupling.

The specific coupling over the total treatment period is ensured by the automation of the procedure of the method steps in accordance with claim 1 and the cyclic repetition or triggering of the method steps a. to c. associated therewith with recognizable problems with the pressure measurement, e.g. by a coupling test or by analysis of the pressure pulse variance at the sensor or also other error cases. A failure of the pressure measurement or a drift toward higher pressures which can otherwise be observed over a longer time period can be prevented in accordance with the invention. A sufficient overpressure can be produced in the measuring chamber by means of the method in accordance with the invention at any time, whereby a good connection to the pressure sensor is achieved. Apart from this, the method can be carried out reliably and fast at any point in time and at any pressure point.

Provision is made in a preferred embodiment of the method for the increase in the pressure in the measuring chamber to be carried out by means of a pump located in the system, in particular by means of a blood pump in the extracorporeal circuit. Provision can be made in this respect for the pump to be operated in reverse operation for the purpose of increasing the pressure in the measuring chamber, that is, in a conveying direction which is opposite to the conveying direction in normal operation. This is, however, not a compulsory feature. If the pressure measuring device is in the region which is on the pump pressure side in normal operation of the pump, a reversal of the conveying direction of the pump is not necessary.

Provision is made in a further embodiment of the operation for a clamp to be closed before or during the operation of the pump to prevent a flow through the system or to oppose the throughflow by an increased resistance, with the clamp being arranged such that the measuring chamber is located between the pump and the clamp.

Provision is made in a further embodiment of the invention for step a. to be carried out before step b. or also for step b. to be carried out before step a. Provision is preferably made for the increase in the pressure of the measuring chamber to a pressure value or the fixing of such a pressure value to take place before the membrane of the measuring chamber is removed from the pressure sensor. it is, however, likewise generally conceivable first to remove the membrane of the measuring chamber from the pressure sensor and then to carry out the increase or fixing of the pressure in the measuring chamber. Provision could be made in this case for a preset volume of the fluid to be conveyed into the measuring chamber.

In accordance with a further embodiment of the invention, provision is made for the increase in the pressure to be carried out until a preset pressure value or pressure value range has been reached. If this is not the case, provision can be made for the pump to continue to convey until the pressure value has been reached. If the pressure value has been reached, provision can still be made for the pump to be stopped.

Provision is made in a further embodiment of the invention for the pump to take place for the purpose of the pressure increase, starting from a defined position of the conveying member of the pump. It is in particular sensible in the case of the use of a peristaltic pump advantageously to carry out the launching of an overpressure from a defined position of the rotor so that the enclosed negative pressure in the pump segment between the rollers does not prevent or impede the desired production of overpressure.

Provision is made in a further embodiment of the invention for the pump to convey for the purpose of the pressure increase for so long until a preset conveying volume or a preset position of the conveying member of the pump has been reached. It is, for example, conceivable in the case of the named peristaltic pump to check the angle of rotation of the rotor and to stop the conveying as soon as a specific angle of rotation has been reached.

Provision is made in a further embodiment of the invention for the pressure in the measuring chamber is measured in each case before step b., that is before the separation of the membrane of the measuring chamber from the pressure sensor and after step c., that is after the reconnection, and for an error message to be output if the two pressure values do not coincide or if they are not in a preset range. It is conceivable for the named pressure measurements to be carried out directly before the decoupling and after the recoupling.

Provision is made in a further embodiment of the invention for the clamp to be opened when the membrane of the measuring chamber and the pressure sensor are joined together in accordance with step c.

It is conceivable to measure the pressure in the measuring chamber in each case before the closing of the clamp against which the pump conveys and after the named opening of the clamp and to output an error message if the two pressure values do not coincide or are not in a preset range.

Provision is made in a further embodiment of the invention for the pressure sensor to be subjected to a function test after the separation of the membrane of the measuring chamber from the pressure sensor in accordance with step b. and before the joining together of the membrane of the measuring chamber and of the pressure sensor in accordance with step c. Any required test of the pressure sensor can thus optionally be carried out by the cyclic starting up of the pressure sensor device. The pressure sensor can be switched for a brief time against the environment or against a reference pressure in the non-coupled state and can be checked with respect to its zero point or a reference point and thus with respect to its function.

The present invention furthermore relates to an apparatus having the features of claim 14.

Accordingly, first means are provided for increasing the pressure in the measuring chamber to a pressure value at which the membrane is at least slightly outwardly curved relative to the measuring chamber in the state not connected to the pressure sensor or for determining such a pressure value. The apparatus furthermore has second means for the separation of the membrane of the measuring chamber from the pressure sensor as well as third means for the joining together of the membrane of the measuring chamber and of the pressure sensor such that the membrane of the measuring chamber contacts the pressure sensor. The apparatus furthermore has a control unit which is made such that it controls the first, second and third means in accordance with their designated operations without any intervention of the staff at predetermined time intervals and/or on the occurrence of an error case.

The apparatus furthermore has means for the carrying out of the method steps in accordance with one of the claims 1 to 13.

Preferred embodiments of the apparatus are the subject of claims 15 to 27.

In a preferred embodiment of the invention, the measuring chamber is made as a disposable product or as a component of a disposable product. It is thus conceivable to replace the measuring chamber after the treatment of a patient. Provision is preferably further made for the pressure sensor to be made as a reusable part or as a component of a reusable unit, that is, for it anyway not to be replaced after each treatment, but only as required.

The present invention furthermore relates to a unit, in particular to a medical unit having the features of claim 28. The unit can, for example, be a dialyzer, a device to support the liver or a device of apheresis treatment.

The present invention furthermore relates to the use of a measuring chamber which is bounded by a flexible membrane and which preferably has a fluid inflow and a fluid outflow as a component of a pressure measuring device in a method in accordance with one of the claims 1 to 13 and/or in an apparatus in accordance with one of the claims 14 to 27 and/or in a unit in accordance with one of the claim 28 or 29.

As stated above, provision can be made for the measuring chamber to be made as a disposable product and to be discarded after conclusion of preferably one treatment.

Figure 2:
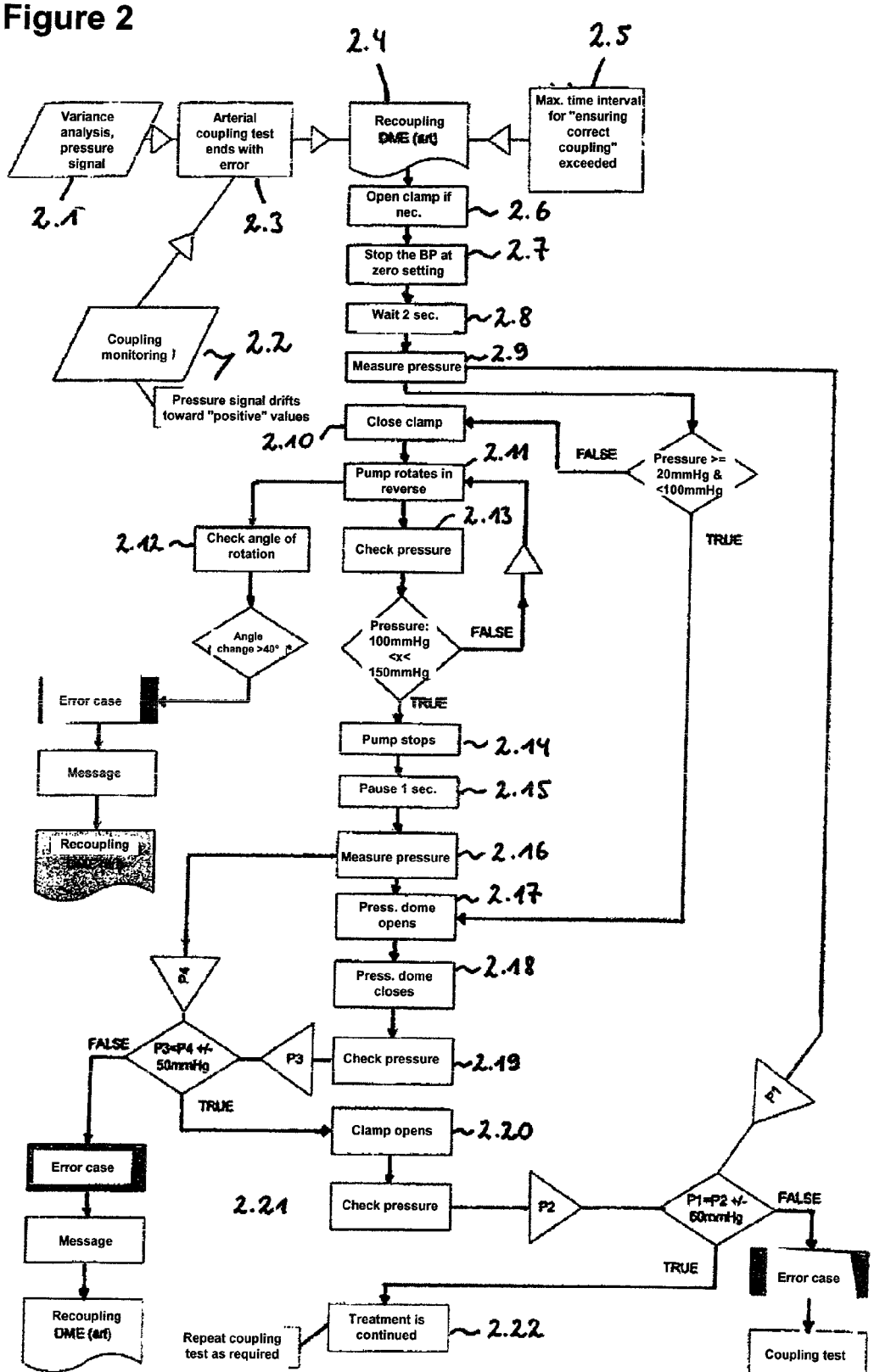

Further details and advantages of the invention will be explained in more detail with reference to an embodiment shown in the drawing. There are shown:

FIG. 1: a schematic representation of the procedure of the recoupling of the membrane of the measuring chamber to the pressure sensor in accordance with the present invention; and FIG. 2: a flow diagram for the carrying out of the recoupling of the membrane of the measuring chamber to the pressure sensor in accordance with the present invention, with all the figure values given only having the character of examples.

FIG. 1a shows a pressure measuring device with the reference numeral 10 for the measurement of the pressure of an extracorporeal circuit 20 of a dialyzer. A blood pump located in the extracorporeal circuit 20 is marked by the reference numeral 30. Reference numeral 40 characterizes a clamp by means of which the hose line of the extracorporeal circuit 20 can be blocked.

As can be seen from FIG. 1a, the pressure measuring device 10 is located between the named clamp 40 and the blood pump 30 in the extracorporeal circuit 20 of a dialyzer. In normal operation, the blood pump 30 conveys in the arrow direction in accordance with FIG. 1a which, in other words, means that the pressure measuring device 10 is on the suction side of the blood pump 30. In normal operation, comparatively low pressures can thus occur in the measuring chamber 12, which is indicated in the FIGS. 1b to 1e, and the risk of the decoupling of the membrane 13 from the pressure sensor 14 likewise shown in FIGS. 1b to 1e is increased at said low pressures.

Provision is made in accordance with the embodiment shown here for a decoupling, that is a separation of the membrane 13 of the measuring chamber 12 from the pressure sensor 14 to take place at predetermined time intervals, that is, periodically, or in the case of an error and subsequently a recoupling of the membrane 13 of the measuring chamber 12 to the pressure sensor 14. A good mechanical contact is furthermore ensured by this recoupling. The treatment can then be continued normally, whereas it is preferably interrupted during the decoupling and coupling process. If a recoupling is provided, for instance because a predetermined time period has expired or because an error case has been found, for example the unwanted release of the membrane 13 from the pressure sensor 14, the blood pump 30 is stopped, starting from the state in accordance with FIG. 1a, and the clamp 40 is closed, as is shown in FIG. 1b. In accordance with FIG. 1c, the blood pump is then operated in reverse, that is, against the normal conveying direction, whereby a throughflow in the arrow direction in accordance with FIG. 1c results. An overpressure or a pressure build-up thus occurs in the measuring chamber 12 of the pressure measuring device 10 due to the closed clamp 40. Provision can be made in this respect for the pressure build-up to be restricted in its amount for safety reasons. Alternatively or additionally, provision can be made to monitor the angle of rotation of the blood pump 30 made as a peristaltic pump and/or to detect the conveyed volume. The rearward running of the blood pump 30 is preferably carried out until a sufficient pressure is built up.

To prevent the enclosed negative pressure in the pump segment between the rollers from impeding or preventing the desired production of overpressure in the case of a peristaltic pump, provision is made in accordance with the embodiment shown here for the starting up of the pump 30 or the starting of the build-up of the overpressure in the measuring chamber 12 to take place from a defined position of the rotor of the pump 30.

If the desired pressure value in the measuring chamber 12 has been reached, in accordance with step 1d, the pressure measuring device 10 is opened, which means, in other words, that the membrane 13 of the measuring chamber 12 is separated from the pressure sensor 14. The membrane 13 of the measuring chamber is outwardly curved due to the overpressure prevailing in the measuring chamber 12, as is indicated in FIG. 1d. A bulging of the membrane 13 of the measuring chamber 12 accordingly occurs.

Then, in accordance with step 1e, a recoupling is carried out, that is, the convexly shaped membrane 13 is placed onto the pressure sensor 14.

After carrying out a coupling test in which it can be determined whether the coupling has taken place reliably, provision can be made for the clamp 40 to be opened again and for the blood pump 30 again to be operated in its normal conveying direction in accordance with FIG. 1a.

FIG. 2 shows an exemplary flow diagram that describes the recoupling of the membrane 13 of the measuring chamber 12 to the pressure sensor 14 in accordance with the invention. In accordance with a step 2.1, a variance analysis of the pressure signal can take place or, in accordance with step 2.2., a test of the time development of the pressure signal can be carried out. If these checks end with an error in accordance with step 2.3, a recoupling in accordance with step 2.4 is initiated.

Alternatively or additionally, provision can be made for the recoupling in accordance with step 2.4 to be carried out in accordance with step 2.5 after the expiration of a time interval which can typically be approximately $\geq$12 hours depending on the circumstance.

The recoupling starts in that, in accordance with step 2.6, the clamp is opened, where necessary, and in that subsequently, in accordance with step 2.7, the blood pump 30 is stopped at a preferred position which is shown as the zero position here. After the end of a waiting period of, for example, 2 seconds in accordance with step 2.8, the pressure in the measuring chamber 12 is measured in step 2.9. If this is above a limit value or in a predetermined range which is between 20 mmHg and 100 mmHg in the embodiment shown here, a decoupling of the membrane 13 of the measuring chamber 21 from the pressure sensor 14 is carried out.

If this is, however, not the case, it is determined that a pressure increase in the measuring chamber 12 must be carried out. In this case, the clamp is closed (step 2.10) and the blood pump 30 is operated in reverse (step 2.11). The angle of rotation of the pump is checked in step 2.12. If an unwanted angular change occurs, an error message is output. The recoupling can then be started again.

The pressure is checked after the start-up of the pump 30 (step 2.13). If it is found that the pressure is in a preset pressure value range, the pump is stopped (step 2.14). If this is not the case, the pump is operated further.

After the stopping of the blood pump 30, a wait of a predetermined time duration, here one second, is carried out (step 2.15) and the pressure is then measured (step 2.16). This pressure value is shown in FIG. 2 as P4. In step 2.17, the so-called pressure dome is opened, which means, in other words, that the membrane 13 of the measuring chamber 12 is removed from the pressure sensor 14. Subsequently, a recoupling is carried out ("pressure dome closes" in step 2.18) and the pressure is then checked (step 2.19). This pressure measurement value is marked by P3 in FIG. 2. If the pressure values P3 and P4 do not coincide within a tolerance band, an error message is output and the recoupling is restarted. If this is, however, not the case, the clamp is opened again (step 2.20) and the pressure in the measuring chamber 12 is then checked again (step 2.21). The pressure value determined in this process is marked by P2 in FIG. 2. If the pressure P1 measured before the closing of the clamp does not coincide with the pressure P2 within a tolerance band, an error case is reported and the so-called coupling test is carried out.

If, however, both pressure values coincide within the tolerance band, the treatment is continued, that is the pump is set into operation in its normal conveying direction and the treatment is continued (step 2.22).

It is ensured by the present invention that a decoupling of the membrane 13 of the measuring chamber 12 from the pressure sensor 14 is precluded over a long time period or can also be corrected with a negative pressure prevailing in the extracorporeal circuit 20. Reliable pressure measurements are thereby ensured.

The present invention is in particular of importance when the pressure measurement takes place in a range which is on the negative pressure side, that is, on the suction side of a pump, in normal operation and in which a negative pressure can also prevail with a stopped liquid pump. The invention is, however, not restricted to this and also includes cases in which the pressure measuring device is on the pressure side of a pump.

The method in accordance with the invention or the apparatus in accordance with the invention can be used, for example, in a multifunctional unit for the treatment of acute kidney diseases and/or for use in liver support and/or for use in various therapeutic apheresis processes. Other application cases are also conceivable.

The pressure sensor 14, as also the measuring chamber 12, can be made with a membrane which the membrane 13 of the measuring chamber 12 contacts in normal operation. An arrangement is, for example, conceivable such as is known from U.S. Pat. No. 5,614,677; reference is hereby made to the disclosure content of this reference to this extent.

The invention claimed is:
1. A method for the operation of a pressure measuring device (10) for the measurement of the pressure in a system through which fluid flows, in particular in an extracorporeal circuit (20) of a medical unit, with the pressure measuring device (10) having a measuring chamber (12) which is bounded by a flexible membrane (13), through which fluid flows in the operation of the system or which is filled with fluid and also having a pressure sensor (14) connected to the membrane (13) for the purpose of pressure measurement, characterized in that the method includes the following steps not requiring any intervention of the staff:

a. increasing the pressure in the measuring chamber (12) to a pressure value at which the membrane (13) is at least slightly outwardly curved relative to the measuring chamber (12) in the state not connected to the pressure sensor (14) or determining such a pressure value;

b. separating the membrane (13) of the measuring chamber (12) from the pressure sensor (14);

c. joining together the membrane (13) of the measuring chamber (12) and of the pressure sensor (14) such that the membrane (13) of the measuring chamber (12) contacts the pressure sensor (14); and d. repeating the steps a, to c, at predetermined intervals and/or on the occurrence of an error case.

2. A method in accordance with claim 1, characterized in that the increase in the pressure in the measuring chamber (12) is carried out by means of a pump (30) located in the system, in particular by means of a blood pump (30) located in the extracorporeal circuit (20).

3. A method in accordance with claim 2, characterized in that the pump (30) is operated in reverse operation for the purpose of increasing the pressure in the measuring chamber (12).

4. A method in accordance with claim 2, characterized in that a clamp (40) is closed before or after the operation of the pump (30) to prevent the system being flowed through or to set an increased resistance against the throughflow, with the clamp (40) being arranged such that the measuring chamber (12) is located between the pump (30) and the clamp (40).

5. A method in accordance with claim 4, characterized in that the clamp (40) is opened when the membrane (13) of the measuring chamber (12) and the pressure sensor (14) are joined together in accordance with step c.

6. A method in accordance with claim 5, characterized in that the pressure in the measuring chamber (12) is measured before the closing of the clamp (40) and after the opening of the clamp (40); and in that an error message is output if the pressure values do not coincide or if they are not in a preset range.

7. A method in accordance with claim 2, characterized in that the pump (30) is set into operation for the purpose of the pressure increase, starting from a defined position of the conveying member of the pump (30).

8. A method in accordance with claim 2, characterized in that the pump (30) conveys so long for the purpose of the pressure increase until a preset conveying volume has been reached or until a preset position of the conveying member of the pump (30) has been reached.

9. A method in accordance with claim 1, characterized in that step a, is carried out before step b, or step b, is carried out before step a.

10. A method in accordance with claim 1, characterized in that the increase of the pressure is carried out until a predetermined pressure value or pressure value range has been reached.

11. A method in accordance with claim 10, characterized in that the pump (30) is stopped when the preset pressure value or pressure value range has been reached.

12. A method in accordance with claim 1, characterized in that the pressure in the pressuring chamber (1) is measured before step b, and after step c.; and in that an error message is output if the pressure values do not coincide or if they are not in a preset range.

13. A method in accordance with claim 1, characterized in that the pressure sensor (14) is subjected to a function test after the separation of the membrane (13) of the measuring chamber (12) from the pressure sensor (14) in accordance with step b, and before the joining together of the membrane (13) of the measuring chamber (12) and of the pressure sensor (14) in accordance with step c.

14. Use of a measuring chamber (12) bounded by a flexible membrane (13) and having a fluid inflow and a fluid outflow as a component of a pressure measuring device (10) in a method in accordance with claim 1.

15. Use in accordance with claim 14, characterized in that the measuring chamber (12) is made as a disposable product and is discarded after the conclusion of preferably one treatment.

16. An apparatus having at least one pressure measuring device (10) for the measurement of the pressure in a system through which fluid flows, in particular in an extracorporeal circuit (20) of a medical unit, with the pressure measuring device (10) having at least one measuring chamber (12) which is bounded by a flexible membrane (13), through which fluid flows in the operation of the system or which is filled with fluid and also having at least one pressure sensor (14) connected to the membrane (13) for the purpose of pressure measurement, characterized in that the apparatus has first means for increasing the pressure in the measuring chamber (12) to a pressure value at which the membrane (13) is at least slightly outwardly curved relative to the measuring chamber (12) in the state not connected to the pressure sensor (14), or for determining such a pressure value; second means for separating the membrane (13) of the measuring chamber (12) from the pressure sensor (14); third means for joining together the membrane (13) of the measuring chamber (12) and of the pressure sensor (14) such that the membrane (13) of the measuring chamber (12) contacts the pressure sensor (14) as well as a control unit which is made such that it controls the first, second and third means at predetermined time intervals and/or on the occurrence of an error case without intervention of the staff.

17. An apparatus in accordance with claim 16, characterized in that the first means include a pump (30), in particular a blood pump (30) located in the extracorporeal circuit (20).

18. An apparatus in accordance with claim 17, characterized in that the control unit is made such that it controls the pump (30) for the purpose of increasing the pressure in the measuring chamber (12) in reverse operation.

19. An apparatus in accordance with claim 17, characterized in that the control unit is made such that it initiates the increase of the pressure in the measuring chamber (12) by the pump (30), starting from a defined position of the conveying member of the pump (30).

20. An apparatus in accordance with claim 17, characterized in that the control unit is made such that it initiates the increase of the pressure in the measuring chamber (12) by the pump (30) until a preset conveying volume has been reached or until a preset position of the conveying member of the pump (30) has been reached.

21. An apparatus in accordance with claim 16, characterized in that the first means include a clamp (40) to prevent a throughflow of the system or to set an increased resistance against the throughflow of the system, with the clamp (40) being arranged such that the measuring chamber (12) is located between the pump (30) and the clamp (40), and wherein the control unit is made such that it initiates the partial or complete closing of the clamp (40) before or while the pump (30) runs for the purpose of increasing the pressure in the measuring chamber (12).

22. An apparatus in accordance with claim 21, characterized in that the control unit is made such that it in each case initiates a pressure measurement in the measuring chamber (12) before the closing of the clamp (40) and after the opening of the clamp (40); and in that a device is provided for the outputting of an error message which is made such that it is activated by the control unit if the two pressure values do not coincide or are not in a preset range.

23. An apparatus in accordance with claim 16, characterized in that the control unit is made such that it controls the first and second means such that the first means are operated before the second means or the second means are operated before the first means.

24. An apparatus in accordance with claim 16, characterized in that the control unit is made such that it initiates an increase in the pressure in the measuring chamber (12) by the first means until a preset pressure value or pressure value region has been reached.

25. An apparatus in accordance with claim 16, characterized in that the control unit is made such that it in each case initiates a pressure measurement in the measuring chamber (12) before activation of the second means and after activation of the third means; and in that a device is provided for the outputting of an error message which is made such that it is activated by the control unit if the two pressure values do not coincide or are not in a preset range.

26. An apparatus in accordance with claim 16, characterized in that the control unit is made such that it initiates the opening of the clamp (40) after the membrane (13) of the measuring chamber (12) and the pressure sensor (14) have been joined together by the third means.

27. An apparatus in accordance with claim 16, characterized in that the control unit is made such that it subjects the pressure sensor (14) to a function test after the activation of the second means and before the activation of the third means.

28. An apparatus in accordance with claim 16, characterized in that the measuring chamber (12) is made as a disposable product or is a component of a disposable product.

29. An apparatus in accordance with claim 16, characterized in that the pressure sensor (14) is made as a reusable part or as a component of a reusable unit.

30. A unit, in particular a medical unit, comprising at least one apparatus in accordance with claim 16.

31. A unit in accordance with claim 30, characterized in that it is a dialyzer, a unit to support the liver or a unit for apheresis treatment.

32. Use of a measuring chamber (12) bounded by a flexible membrane (13) and having a fluid inflow and a fluid outflow as a component of a pressure measuring device (10) in a unit in accordance with claim 30.

33. Use of a measuring chamber (12) bounded by a flexible membrane (13) and having a fluid inflow and a fluid outflow as a component of a pressure measuring device (10) in an apparatus in accordance with claim 16.

* * * * *